United States Patent [19]

Chaloner-Gill et al.

[11] Patent Number: 5,648,185
[45] Date of Patent: Jul. 15, 1997

[54] ALLYL SILANE MONOMERS AND SOLID ELECTROLYTES DERIVED BY POLYMERIZATION THEREOF

[75] Inventors: Benjamin Chaloner-Gill, Santa Clara; Neal Golovin, San Jose, both of Calif.

[73] Assignee: Valence Technology, Inc., Henderson, Nev.

[21] Appl. No.: 49,203

[22] Filed: Apr. 19, 1993

[51] Int. Cl.$^6$ .................................................. H01M 10/26
[52] U.S. Cl. .................................................. 429/192; 252/62.2
[58] Field of Search ........................... 429/192; 252/62.2; 528/392, 425; 556/416, 444, 445, 458

[56] References Cited

U.S. PATENT DOCUMENTS 4,083,861  4/1978  Seiler et al. .
5,037,712  8/1991  Shackle et al. .
5,091,274  2/1992  Hsiue et al. .............. 429/192

OTHER PUBLICATIONS

Chemical Abstract CA 107(25): 236028u 1987 (month n/a).

Hosomi et al CA 107 (25):236028u, Chem. Phar. Bull., 35(5), 2155–7, 1987 "Pentacoordinate silicon compounds in synthesis: regiospecific alkylation of aldehydes using tri-alkoxy–substituted alkylsilane, pyrocetechol, and an amine". (month n/a).

*Primary Examiner*—M. Nuzzolillo
*Attorney, Agent, or Firm*—Charles H. Jew

[57] ABSTRACT

This invention is directed to novel allyl silane monomers and to solid electrolytes containing a solid polymeric matrix having incorporated therein allyl silane monomers. The solid electrolytes are used in electrolytic cells.

15 Claims, No Drawings

ALLYL SILANE MONOMERS AND SOLID ELECTROLYTES DERIVED BY POLYMERIZATION THEREOF

BACKGROUND OF THE INVENTION

1. Field of the Invention

This invention is directed to novel allyl silanes as well as to solid electrolytes derived by polymerization of such allyl silanes.

This invention is further directed to solid electrolytic cells (batteries) containing an anode, a cathode and a solid electrolyte containing a solvent and a polymer matrix which includes allyl silane repeating units.

2. State of the Art

Electrolytic cells containing an anode, a cathode and a solid, solvent-containing electrolyte are known in the art and are usually referred to as "solid batteries". These cells offer a number of advantages over electrolytic cells containing a liquid electrolyte (i.e., "liquid batteries") including improved safety features.

The solid, solvent-containing electrolyte employed in such solid batteries has heretofore contained either an inorganic matrix or an organic polymeric matrix as well as a suitable inorganic ion salt. Because of their expense and difficulty in forming into a variety of shapes, inorganic non-polymeric matrices are, however, not preferred and the art typically has employed a solid electrolyte containing an organic or inorganic polymeric matrix.

Suitable organic polymeric matrices are well known in the art and are typically organic homopolymers obtained by polymerization of a suitable organic monomer as described, for example, in U.S. Pat. No. 4,908,283 or copolymers obtained by polymerization of a mixture of organic monomers.

Additionally, suitable organic monomers preferably contain at least one heteroatom capable of forming donor acceptor bonds with inorganic cations (e.g., alkali ions). When polymerized, these compounds form a polymer suitable for use as an ionically conductive matrix in a solid electrolyte.

The solid electrolytes also contain an electrolyte solvent (plasticizer) which is added to the matrix primarily in order to enhance the solubility of the inorganic ion salt in the solid electrolyte and thereby increase the conductivity of the electrolytic cell. In this regard, the solvent requirements of the solvent used in the solid electrolyte have been art recognized to be different from the solvent requirements in liquid electrolytes. For example, solid electrolytes require a lower solvent volatility as compared to the solvent volatilities permitted in liquid electrolytes.

Suitable electrolyte solvents well known in the art for use in such solid electrolytes include, by way of example, propylene carbonate, ethylene carbonate, γ-butyrolactone, tetrahydrofuran, glyme (dimethoxyethane), diglyme, tetraglyme, dimethylsulfoxide, dioxolane, sulfolane and the like.

The solid, solvent-containing electrolyte has typically been formed by one of two methods. In one method, the solid matrix is first formed and then a requisite amount of this material is dissolved in a volatile solvent. Requisite amounts of the inorganic ion salt and the electrolyte solvent (e.g., a mixture of a glyme and an organic carbonate) are then added to the solution. This solution is then placed on the surface of a suitable substrate (e.g., the surface of a cathode) and the volatile solvent is removed to provide for the solid electrolyte.

In the other method, a monomer or partial polymer of the polymeric matrix to be formed is combined with appropriate amounts of the inorganic ion salt and the electrolyte solvent. This mixture is then placed on the surface of a suitable substrate (e.g., the surface of the cathode) and the monomer is polymerized or cured (or the partial polymer is then further polymerized or cured) by conventional techniques (e.g., heat, ultraviolet radiation, electron beams, etc.) so as to form the solid, solvent-containing electrolyte.

While the electrolytes described above perform adequately in their intended role, there is need for improvement in several areas. First, the conductivity of the electrolytes could advantageously be increased. Better conductivity provides improved charge transference and hence greater cumulative capacity, which is defined as the summation of the capacity of the battery over each cycle (charge and discharge) in a specific cycle life.

Second, the electrolytes must be compatible with the typically used inorganic ion salt incorporated into the polymer matrix to aid in conductivity. The inorganic ion salt, which usually contains Li ion but which can contain other metal ions as defined hereinafter, must be soluble in the electrolyte to form a one-phase system. Hence the amount of salt which can be incorporated in the electrolyte is limited by the salt's saturation concentration. By providing an electrolytic environment in which the salt is more soluble, more of the salt could be incorporated and hence conductivity could be increased.

Third, the solid polymeric matrix of the electrolytes must have a certain degree of flexibility and swellability in order to function properly in the cell. If the cross-linking density of the matrix is too high, the resulting polymer network is very tight, resulting in minimal flexibility and swellability.

SUMMARY OF THE INVENTION

The present invention is directed, in part, to the discovery of novel allyl silane monomers which can be incorporated into the backbone of an ionically conductive polymer matrix. The allyl silanes of the invention provide improvements in conductivity, compatibility, and in the mechanical properties of flexibility and swellability. The allyl silane monomers of this invention are represented by Formula I:

$$RCH=CHCH_2SiR_1R_2R_3 \qquad I$$

where R is selected from the group consisting of hydrogen and an alkyl group having from 1 to 3 carbon atoms and $R_1$, $R_2$ and $R_3$ are independently selected from the group consisting of $-O(R_4O)_pR_5$, $-NR_6R_7$, $-R_8[OC(O)]_aOR_9$ and $-R_8[OC(O)R_{10}]_bOC(O)R_9$ where $R_4$, $R_8$ and $R_{10}$ are independently an alkylene group of 1 to 4 carbon atoms, $R_5$ and $R_9$ are independently selected from the group consisting of hydrogen, an allyl group, an alkyl group having from 1 to 4 carbon atoms, and an inorganic ion selected from the group consisting of Li, Na, K and Mg, $R_6$ and $R_7$ are independently selected from the group consisting of hydrogen and an alkyl group having from 1 to 4 carbon atoms, a is an integer equal to 1 or 2, b is an integer from 1 to 4, and p is an integer from 0 to 4.

When copolymerized with one or more other monomers such as the organic monomers mentioned above, the allyl silane monomers form a polymer suitable for use as an ionically conductive matrix in a solid electrolyte. Accordingly, in another of its composition aspects, this invention is directed to a single phase, solid, solvent-containing electrolyte which comprises:

a solid polymeric matrix; and a solvent;
wherein the solid polymeric matrix is obtained by copolymerizing an organic monomer represented by Formula I

$$RCH=CHCH_2SiR_1R_2R_3 \quad I$$

where R, $R_1$, $R_2$ and $R_3$ are as defined above, with the proviso that when $R_5$ or $R_9$ is other than the above-described inorganic ion, the electrolyte further includes an ion conducting amount of an inorganic ion salt.

In yet another of its composition aspects, the present invention is directed to an electrolytic cell which comprises:
an anode comprising a compatible anodic material;
a cathode comprising a compatible cathodic material; and
interposed therebetween a solid, solvent-containing electrolyte which comprises:
a solid polymerix matrix; and
an electrolyte solvent;
wherein the solid polymeric matrix is obtained by copolymerizing an organic monomer represented by Formula I $$RCH=CHCH_2SiR_1R_2R_3 \quad I$$

where R, $R_1$, $R_2$ and $R_3$ are as defined above, with the proviso that when $R_5$ or $R_9$ is other than the above-described inorganic ion, the electrolyte further includes an ion conducting amount of an inorganic ion salt.

Preferably, $R_1$, $R_2$ and $R_3$ are each $-OCH_2CH_3$, $-O(CH_2CH_2O)_3CH_3$ or $-O(CH_2CH_2O)_3Li$.

DETAILED DESCRIPTION OF THE PREFERRED EMBODIMENTS

As noted above, this invention is directed to solid, solvent- containing electrolytes which employ a specific solid, polymeric, ion-conducting matrix. However, prior to describing this invention in detail, the following terms will first be defined.

Definitions

As used herein, the following terms have the following meanings.

The term "solid polymeric matrix" refers to an ion-conductive matrix formed by polymerizing an organic monomer containing at least one heteroatom capable of forming donor acceptor bonds with inorganic cations derived from inorganic ion salts under conditions such that the resulting polymer is useful in preparing solid electrolytes. Solid polymeric matrices are well known in the art and are described, for example, in U.S. Pat. No. 4,908,283 and in U.S. Pat. No. 4,925,751 both of which are incorporated herein by reference in their entirety.

Suitable organic monomers which are copolymerizable with the allyl silanes of the invention include, by way of example, polyethylene oxide, polypropylene oxide, polyethyleneimine, polyepichlorohydrin, polyethylene succinate, the various methane acrylates and an acryloyl-derivatized polyalkylene oxide containing an acryloyl group of the formula $CH_2=CR'C(O)O-$ where R' is hydrogen or lower alkyl of from 1–6 carbon atoms.

The solid polymeric matrices of the present invention includes at least one organic monomer as defined above along with at least one allyl silane monomer.

The term "inorganic ion salt" refers to any ion conducting inorganic salt which is suitable for use in a solid electrolyte. Representative examples are alkali metal salts of less mobile anions of weak bases having a large anionic radius. Examples of such anions are $I^-$, $Br^-$, $SCN^-$, $ClO_4^-$, $BF_4^-$, $PF_6^-$, $AsF_6^-$, $CF_3COO^-$, $CF_3SO_3^-$, etc. Specific examples of suitable inorganic ion salts include $LiClO_4$, $LiI$, $LiSCN$, $LiBF_4$, $LiAsF_6$, $LiCF_3SO_3$, $LiPF_6$, $NaI$, $NaSCN$, $KI$ and the like. The inorganic ion salt preferably contains at least one atom of Li, Na, K or Mg.

The term "electrolyte solvent" refers to the solvent (i.e., plasticizer) added to the electrolyte and/or the cathode for the purpose of solubilizing the inorganic ion salt. Preferred are the various polar aprotic solvents. Examples of polar aprotic solvents useful in the invention are polar solvents such as propylene carbonate, ethylene carbonate, butylene carbonate, γ-butyrolactone, tetrahydrofuran, 2-methyltetrahydrofuran, and 1,3-dioxolane.

In a preferred embodiment, the electrolyte solvent is a mixture of propylene carbonate and a glyme in a ratio (w/w) of from about 10:1 to about 1:4. In a highly preferred embodiment, the ratio is 4:1 propylene carbonate/triglyme.

If the solid polymeric matrix is formed by radiation polymerization of the monomer of Formula I, then the solvent should be radiation inert at least up to the levels of radiation employed. If the solid polymeric matrix is formed by thermal polymerization, the solvent should be thermally inert at least up to the temperatures of thermal polymerization. Additionally, the solvent should not scavenge free radicals.

A particularly preferred solvent is a mixture of an organic carbonate and triglyme as disclosed in U.S. patent application Ser. No. 07/918,509, filed Jul. 22, 1992, and entitled "SOLID, SOLVENT-CONTAINING ELECTROLYTES AND ELECTROLYTIC CELLS PRODUCED THEREFROM" which application is incorporated herein by reference in its entirety.

The term "cured" or "cured product" refers to the treatment of the monomer of Formula I above (or partial polymer thereof) under polymerization conditions (including crosslinking) so as to form a solid polymeric matrix. Suitable polymerization conditions are well known in the art and include, by way of example, heating the monomer, irradiating the monomer with UV light, electron beams, etc.

The term "ion salt derivative" refers to ions of the formulae $-O(R_4O)_pR_5$, $-R_8[OC(O)_a]OR_9$ and $-R_8[OC(O)R_{10}]_bOC(O)R_9$ where $R_4$, $R_8$, a, b and p are as defined above, and $R_5$ and $R_9$ are each an inorganic ion which can be, for example, Li, Na, K or Mg.

The term "electrolytic cell" refers to a composite containing an anode, a cathode, and an ion-conducting electrolyte interposed therebetween.

The anode is typically comprised of a compatible anodic material which is any material which functions as an anode in a solid electrolytic cell. Such compatible anodic materials are well known in the art and include, by way of example, lithium, lithium alloys, such as alloys of lithium with aluminum, mercury, manganese, iron, zinc, and the like, and intercalation based anodes such as carbon, tungsten oxides, and the like.

The cathode is typically comprised of a compatible cathodic material (i.e., insertion compounds) which is any material which functions as a positive pole in a solid electrolytic cell. Such compatible cathodic materials are well known in the art and include, by way of example, manganese oxides, molybdenum oxides, vanadium oxides, sulfides of titanium, molybdenum and niobium, the various chromium oxides, copper oxides, lithiated cobalt oxides, lithiated manganese oxides, and the like. The particular compatible cathodic material employed is not critical.

In one preferred embodiment, the compatible cathodic material is mixed with an electroconductive material including, by way of example, graphite, powdered carbon, powdered nickel, metal particles, conductive polymers (i.e., characterized by a conjugated network of double bonds like polypyrrole and polyacetylene), and the like, and a polymeric binder to form under pressure a positive cathodic plate.

In another preferred embodiment, the cathode is prepared from a cathode paste which comprises from about 35 to 65 weight percent of a compatible cathodic material; from about 1 to 20 weight percent of an electroconductive agent; from about 0 to 20 weight percent of polyethylene oxide having a number average molecular weight of at least 100,000; from about 10 to 50 weight percent of the electrolyte solvent; and from at least about 5 weight percent to 30 weight percent of a solid polymeric matrix which includes the monomer of Formula I above. (All weight percents are based on the total weight of the cathode.)

The cathode paste is typically spread onto a suitable support such as a current collector and then cured by conventional methods to provide for a solid positive cathodic plate. The cathode (excluding the support) generally has a thickness of from about 20 to about 150 microns.

Current collectors are well known in the art some of which are commercially available. One particularly preferred current collector for the cathode is a toughened nickel (electrolytically deposited nickel) on nickel current collector (available as CF18/NiT from Fukuda Metal Foil & Powder Company, Ltd., Kyoto, Japan). Another preferred current collector employs a sheet of aluminum foil. The current collector is preferably attached to the surface of the cathode not facing the electrolyte but can also be attached to the anode. When the current collector is attached to the cathode, the cathode is interposed between the electrolyte and the current collector.

In still another preferred embodiment, the electrolyte solvent and the cathode solvent are identical.

The term "urethane acrylate" refers to urethane diacrylate.
Methodology

Methods for preparing solid electrolytes are well known in the art. This invention, however, utilizes a particular monomer in the preparation of solid polymeric matrix used in the solid electrolytes, which monomer is represented by Formula I:

$$RCH=CHCH_2SiR_1R_2R_3 \qquad I$$

where R, $R_1$, $R_2$ and $R_3$ are as defined above.

The monomers of Formula I above are readily prepared by reacting a halosilane (typically a chlorosilane) with a hydroxy- or amine-terminated group corresponding to $R_1$, $R_2$ or $R_3$. The reaction results in the evolution of hydrogen halide (e.g., HCl) and the bonding of the residual alkoxy or amine group to the silicon atom. The number of substitutions on the silicon is a function of the degree of halosubstitution on the silane starting material.

In a first embodiment, the solid, solvent-containing electrolyte is then prepared by combining a compound of Formula I or a mixture of compounds of Formula I and at least one other organic monomer or partial polymer with an inorganic ion salt and the electrolyte solvent. The resulting composition is then uniformly coated onto a suitable substrate (e.g., aluminum foil, a glass plate, a lithium anode, a cathode, etc.) by means of a roller, a doctor blade, a bar coater, a silk screen or spinner to obtain a film of this composition or its solution. In some cases, it may be necessary to heat the composition so as to provide for a coatable material.

Preferably, the amount of material coated onto the substrate is an amount sufficient so that after curing, the resulting solid, solvent-containing electrolyte has a thickness of no more than about 250 microns (μm). Preferably, the solid, solvent-containing electrolyte has a thickness of from about 25 to about 100 microns. The actual thickness chosen is a function of the particular application and can readily be determined by one skilled in the art.

The electrolyte composition typically comprises from about 5 to about 25 weight percent of an inorganic ion salt based on the total weight of the electrolyte, preferably, from about 10 to about 20 weight percent, and even more preferably about 15 weight percent.

In an alternative embodiment, rather than being added as a separate component in the form of an inorganic ion salt, an inorganic ion as described above, such as a lithium ion, is incorporated into one or more compounds (e.g. alcohols) containing the groups $R_1$, $R_2$ and $R_3$. The thus formed ion salt derivative is then reacted with a halosilane to attach the pendent groups $R_1$, $R_2$ and $R_3$ to the silicon atom. A preferred group for attachment of inorganic ion is a polyalkylene ether glycol having the formula $HO(R_4O)_pOR"$, or an aliphatic carbonate having the formula $HOR_8[OC(O)]_aOR"$ or the formula $HOR_8[OC(O)R_{10}]_6OC(O)OR"$, where $R_4$, $R_8$, $R_{10}$, a, b and p are as defined above, and R" is H or —$CH_3$. The inorganic ion, in the form of an organometal compound, is reacted with one of the hydroxy groups or a methoxy group of the polyalkylene ether glycol or aliphatic carbonate to form the corresponding ion salt derivative. Other reaction schemes well known to those skilled in the art can alternatively be employed to obtain the ion salt derivative.

Where one or more of $R_1$, $R_2$ and $R_3$ contain an allyl terminal group, the compound of Formula I is capable of forming cross-links in the polymer matrix.

The electrolyte composition typically comprises from about 40 to about 80 weight percent of the electrolyte solvent based on the total weight of the electrolyte, preferably from about 60 to about 80 weight percent, and even more preferably about 70 weight percent.

The solid polymeric matrix can contain up to 99 percent, but typically comprises from about 5 to about 30 percent repeating units derived from a compound of Formula I based on the total number of repeating units in the matrix. Preferably the solid polymeric matrix contains from about 15 to about 25 percent repeating units derived from a compound of Formula I.

The solid polymeric matrix including the allyl silane repeating units can be a random or block copolymer. Formation of blocks of the allyl silane involves the formation of allyl silane dimers, trimers, tetramers, etc. prior to copolymerization with the other organic monomer or monomers.

In a preferred embodiment, the electrolyte composition further comprises a small amount of a film forming agent. Suitable film forming agents are well known in the art and include, by way of example, polypropylene oxide, polyethylene oxide, copolymers thereof, and the like, having a number average molecular weight of at least about 100,000. Preferably, the film forming agent is employed in an amount of from about 1 to about 10 weight percent and more preferably from about 2 to about 4 weight percent based on the total weight of the electrolyte composition.

The composition is cured by conventional methods to form a solid film. For example, suitable curing methods include heating, irradiation with UV radiation, irradiation with electron beams (EB), etc. When the composition is cured by heating or UV radiation, the composition preferably contains an initiator. For example, when curing is by heating, the initiator is typically a peroxide such as benzoyl peroxide, methyl ethyl ketone peroxide, t-butyl peroxypyvarate, diisopropyl peroxycarbonate, and the like. When curing is by UV radiation, the initiator is typically benzophenone, Darocur 1173 (Ciby Geigy, Ardsley, N.Y.), and the like.

The initiator is generally employed in an amount sufficient to catalyze the polymerization reaction. Preferably, the initiator is employed at up to about 1 weight percent based on the weight of the solid matrix forming monomer.

When curing is by EB treatment, an initiator is not required.

The resulting solid electrolyte is a homogeneous, single phase material which is maintained upon curing, and which does not readily separate upon cooling to temperatures below room temperature. See, for example, U.S. Pat. No. 4,925,751 which is incorporated herein by reference in its entirety.

Additionally, it is desirable to avoid the use of any protic materials which will be incorporated into the battery. For example, most of the protic inhibitors for preventing premature monomer polymerization (e.g., protic inhibitors found in di- and triacrylate monomers) employed with the monomers are preferably removed prior to formation of the solid matrix (e.g., the cathode and/or electrolyte) by contact with a inhibitor remover such as Inhibitor Remover available as product number 31,133-2 from Aldrich Chemical, Milwaukee, Wis. Such processes generally will lower the inhibitor concentration to less than about 50 ppm.

In a preferred embodiment, the process of forming an electrolytic cell comprises the steps of coating the surface of a cathode with a composition comprising requisite amounts of a compound of Formula I or a mixture of compounds of Formula I, an inorganic ion salt and the electrolyte solvent. The composition is then cured to provide for a solid electrolyte on the cathodic surface. The anode (e.g., a lithium foil) is then laminated to this composite product in such a way that the solid electrolyte is interposed between the lithium foil and the cathodic material.

This process can be reversed so that the surface of the anode is coated with a composition comprising requisite amounts of a compound of Formula I or a mixture of compounds of Formula I, an inorganic ion salt and the electrolyte solvent. The composition is then cured to provide for a solid electrolyte on the anodic surface. The cathode is then laminated to this composite product in such a way that the solid electrolyte is interposed between the lithium foil and the cathodic material.

Methods for preparing solid electrolytes and electrolytic cells are also set forth in U.S. Pat. Nos. 4,830,939 and 4,925,751 which are incorporated herein by reference in their entirety.

The following examples are offered to illustrate the present invention and should not be construed in any way as limiting its scope.

EXAMPLE 1

A. The Cathode

The cathode may be prepared from a cathodic paste which, in turn, is prepared from a cathode powder as follows:

i. Cathode Powder

The cathode powder is prepared by combining 90.44 weight percent $V_6O_{13}$ [prepared by heating ammonium metavanadate ($NH_4^+VO_3^-$) at 450° C. for 16 hours under N2 flow] and 9.56 weight percent of carbon (from Chevron Chemical Company, San Ramon, Calif. under the trade name of Shawinigan Black®). About 100 grams of the resulting mixture is placed into a grinding machine (Attritor Model S-1 purchased from Union Process, Akron, Ohio) and ground for 45 minutes. Afterwards, the resulting mixture is dried at about 260° C. for 16 hours under vacuum to provide a cathode powder having about 84.45 weight percent $V_6O_{13}$.

The above mixing procedure is repeated until the entire sample is mixed so as to provide for 292 grams of cathode powder.

ii. Cathode Paste

A cathode paste is prepared by combining sufficient cathode powder to provide for a final product having 45 weight percent $V_6O_{13}$.

Specifically, about 26.2 grams of unground carbon (from Chevron Chemical Company, San Ramon, Calif. under the trade name of Shawinigan Black®) is combined in a glove box [under dry (<10 ppm $H_2O$) argon at ambient temperature and pressure] with about 169.9 grams of the 4:1 mixture of propylene carbonate/triglyme and the resulting composite is mixed under dry argon and at ambient temperature and pressure on a double planatory mixer (Ross #2 mixer available from Charles Ross & Sons, Company, Hauppag, N.Y.) at about 25 rpms until a paste is formed.

About 225.0 grams of a cathode powder prepared in a manner similar to that described above is added to the mixer and the resulting composite is mixed under dry argon and at ambient temperature and pressure on a double planatory mixer at about 25 rpms until a dry paste is formed.

About 5 grams of polyethylene oxide (number average molecular weight about 600,000 available as Polyox WSR-205 from Union Carbide Chemicals and Plastics, Danbury, Conn.), about 42.5 grams of polyethylene glycol diacrylate (molecular weight about 400 available as SR-344 from Sartomer Company, Inc., Exton, Pa.) and containing less than about 50 ppm of inhibitor, and about 7.5 grams of ethoxylated trimethylpropane triacrylate (TMPEOTA) (molecular weight about 450, available as SR-454 from Sartomer Company, Inc., Exton, Pa.) and containing less than about 50 ppm of inhibitor, are added to about 169.9 grams of a 4:1 mixture of propylene carbonate/triglyme as described above, and this mixture then added to the mixer.

The resulting slurry in the mixer is heated at about 65° C. while mixing for 2 hours at 60 rpms to provide for the cathodic paste which had the following approximate weight percent of components:

| | |
|---|---|
| $V_6O_{13}$ | 45.00 weight percent |
| Carbon | 10.00 weight percent |
| Propylene carbonate | 27.18 weight percent |
| Triglyme | 6.80 weight percent |
| Polyethylene glycol diacrylate | 8.51 weight percent |
| Ethoxylated trimethylpropane triacrylate[1] | 1.51 weight percent |
| Polyethylene oxide | 1.00 weight percent |

[1]Inhibitor may be removed from both the polyethylene glycol diacrylate and ethoxylated trimethylpropane triacrylate by contacting each of these compounds with an Inhibitor Remover available as Product No. 31,133-2 from Aldrich Chemical, Milwaukee, Wisconsin, which results in less than 50 ppm of inhibitor in the product.

In an alternative embodiment, the requisite amounts of all of the cathodic materials other than the cathode powder can be combined to form a first mixture and this first mixture combined with the cathode powder to form a second mixture. This second mixture is then thoroughly mixed to provide for the cathode paste.

The cathode paste prepared as above is placed onto a sheet [about 1 mil (N-25 μm) thick by 10 cm wide] of a roughened nickel on nickel current collector (available as CF18/NiT from Fukuda Metal Foil & Powder Company, Ltd., Kyoto, Japan). A Mylar cover sheet is then placed over the paste and the paste is spread to a thickness of about 75 microns (μm) with a conventional plate and roller system and cured by continuously passing the sheet through an electron beam apparatus (Electrocurtain, Energy Science Inc., Woburn, Mass.) at a voltage of about 175 kV and a current of about 12 mA and at a conveyor belt speed setting of 50 which provides a conveyor speed of about 3 in/sec. After curing, the Mylar sheet is removed to provide for a solid cathode laminated to a nickel on nickel current collector.

B. Electrolyte

An electrolyte may be prepared by first combining 56.51 grams of propylene carbonate, 14.13 grams triglyme and 10.00 grams of urethane acrylate (available as Photomer 6140 from Henkel Corporation, Coating and Chemicals Division, Ambler, Pa.). The propylene carbonate/triglyme/ urethane acrylate mixture is dried over molecular sieves (Grade 514, 4 Å, 8–12 mesh, available from W. R. Grace, Baltimore, Md.) to remove water. This solution is then combined with 2.56 grams of poly- ethylene oxide (weight average molecular weight about 600,000 available as Polyox WSR-205 from Union Carbide Chemicals and Plastics, Danbury, Conn.) and 7.56 grams of allyl triethoxy silane (an allyl silane monomer of the invention).

The mixture is then thoroughly mixed with the same laboratory mixer at heating until a temperature of about 65° C. is reached and then cooled to ambient temperature over at least a 2 hour period while stirring is maintained.

Once the polyethylene oxide and allyl triethoxy silane are dispersed and dissolved, 9.24 grams of $LiPF_6$ (available from FMC Corporation, Lithium Division, Bessemer City, N.C.) are added while stirring with a laboratory mixer (Yamato Model LR41B, available from Fisher Scientific, Santa Clara, Calif.).

Allyl triethoxy silane can be prepared by reacting 1.0 moles allyl trichlorosilane with 3.1 moles of ethanol. The reaction will proceed with the evolution of gaseous hydrochloric acid. Purification of the allyl triethoxy silane can be performed via vacuum distillation or via a chromatography column.

The resulting mixture would contain the following weight percent of components:

| | |
|---|---|
| Propylene carbonate | 56.51 weight percent |
| Triglyme | 14.13 weight percent |
| Urethane acrylate (Photomer 6140) | 10.00 weight percent |
| $LiPF_6$ | 9.24 weight percent |
| Polyethylene oxide | 2.56 weight percent |
| Allyl triethoxy silane | 7.56 weight percent. |

Afterwards, the electrolyte mixture is then coated by a conventional knife blade to a thickness of about 50 μm onto the surface of the cathode sheet prepared as above (on the side opposite that of the current collector) but without the Mylar covering. The electrolyte is then cured by continuously passing the sheet through an electron beam apparatus (Electrocurtain, Energy Science Inc., Woburn, Mass.) at a voltage of about 1.75 kV and a current of about 1.0 mA and at a conveyor speed setting of 50 which provides for a conveyor speed of about 1 cm/sec. After curing, a composite is recovered which contains a solid electrolyte laminated to a solid cathode which, in turn, is laminated to a nickel on nickel current collector.

C. Anode

The anode may comprise a sheet of lithium foil (about 76 μm thick) which is commercially available from FMC Corporation Lithium Division, Bessemer City, N.C.

D. The Solid Battery

A solid battery may be prepared by first preparing a cathodic paste as described above which is spread onto a substrate (e.g., a current collector) and then cured to provide the cathode. An electrolyte composition as described above is then placed onto the cathode surface and cured to provide for the solid electrolyte. Then, the anode is laminated onto the solid electrolyte to provide for the solid battery.

EXAMPLE 2

A solid electrolytic cell is prepared by first preparing a cathodic paste which is spread onto a current collector and is then cured to provide for the cathode. An electrolyte solution is then placed onto the cathode surface and is cured to provide for the solid electrolyte composition. Then, the anode is laminated onto the solid electrolyte composition to provide for a solid electrolytic cell. The specifics of this construction are as follows:

A. The Current Collector

The current collector employed is a sheet of aluminum foil having a layer of adhesion promoter attached to the surface of the foil which will contact the cathode so as to form a composite having a sheet of aluminum foil, a cathode and a layer of adhesion promoter interposed therebetween.

Specifically, the adhesion promoter layer is prepared as a dispersed colloidal solution in one of two methods. The first preparation of this colloidal solution for this example is as follows:

| | |
|---|---|
| 8.44 | weight percent of carbon powder (Shawinigan Black ® — available from Chevron Chemical Company, San Ramon, CA) |
| 33.76 | weight percent of a 25 weight percent solution of polyacrylic acid (a reported average molecular weight of about 90,000, commercially available from Aldrich Chemical Company — contains about 84.4 grams polyacrylic acid and 253.2 grams water) |
| 57.8 | weight percent of isopropanol. |

The carbon powder and isopropanol are combined with mixing in a conventional high shear colloid mill mixer (Ebenbach-type colloid mill) until the carbon is uniformly dispersed and the carbon particle size is smaller than 10 microns. At this point, the 25 weight percent solution of polyacrylic acid is added to the solution and mixed for approximately 15 minutes. The resulting mixture is pumped to the coating head and roll coated with a Meyer rod onto a sheet of aluminum foil (about 9 inches wide and about 0.0005 inches thick). After application, the solution/foil are contacted with a Mylar wipe (about 0.002 inches thick by about 2 inches and by about 9 inches wide—the entire width of aluminum foil). The wipe is flexibly engaged with the foil (i.e., the wipe merely contacted the foil) to redistribute the solution so as to provide for a substantially uniform coating. Evaporation of the solvents (i.e., water and isopropanol) via a conventional gas-fired oven provides for an electrically-conducting adhesion-promoter layer of about 6 microns in thickness or about $3 \times 10^{-4}$ grams per $cm^2$. The aluminum foil is then cut to about 8 inches wide by removing approximately ½ inch from either side by the use of a conventional slitter so as to remove any uneven edges.

In order to further remove the protic solvent from this layer, the foil is redried. In particular, the foil is wound up and a copper support placed through the roll's cavity. The roll is then hung overnight from the support in a vacuum oven maintained at about 130° C. Afterwards, the roll is removed. In order to avoid absorption of moisture from the atmosphere, the roll is preferably stored into a desiccator or other similar anhydrous environment to minimize atmospheric moisture content until the cathode paste is ready for application onto this roll.

The second preparation of this colloidal solution comprises mixing 25 lbs of carbon powder (Shawinigan Black®— available from Chevron Chemical Company, San Ramon, Calif.) with 100 lbs of a 25 weight percent solution of polyacrylic acid (average molecular weight of about 240,000, commercially available from BF Goodrich, Cleveland, Ohio, as Good-Rite K702—contains about 25 lbs polyacrylic acid and 75 lbs water) and with 18.5 lbs of isopropanol. Stirring is done in a 30 gallon polyethylene drum with a gear-motor mixer (e.g., Lightin Labmaster Mixer, model XJ-43, available from Cole-Parmer Instruments Co., Niles, Ill.) at 720 rpm with two 5 inch diameter A310-type propellers mounted on a single shaft. This wets down the carbon and eliminates any further dust problem. The resulting weight of the mixture is 143.5 lbs and contains some "lumps".

The mixture is then further mixed with an ink mill which consists of three steel rollers almost in contact with each other, turning at 275, 300, and 325 rpms respectively. This high shear operation allows particles that are sufficiently small to pass directly through the rollers. Those that do not pass through the rollers continue to mix in the ink mill until they are small enough to pass through these rollers. When the mixing is complete, the carbon powder is completely dispersed. A Hegman fineness of grind gauge (available from Paul N. Gardner Co., Pompano Beach, Fla.) indicates that the particles are 4–6 µm with the occasional 12.5 µm particles. The mixture can be stored for well over 1 month without the carbon settling out or reagglomerating.

When this composition is to be used to coat the current collector, an additional 55.5 lbs of isopropanol is mixed into the composition working with 5 gallon batches in a plastic pail using an air powered shaft mixer (Dayton model 42231 available from Granger Supply Co., San Jose, Calif.) with a 4 inch diameter Jiffy-Mixer brand impeller (such as an impeller available as Catalog No. G-04541-20 from Cole Parmer Instrument Co., Niles, Ill.). Then, it is gear pumped through a 25 µm cloth filter (e.g., So-Clean Filter Systems, American Felt and Filter Company, Newburgh, N.Y.) and Meyer-rod coated as described above.

B. The Cathode

The cathode is prepared from a cathodic paste which, in turn, is prepared from a cathode powder as follows:

i. Cathode Powder

The cathode powder is prepared by combining 90.44 weight percent $V_6O_{13}$ [prepared by heating ammonium metavanadate ($NH_4^+VO_3^-$) at 450° C. for 16 hours under $N_2$ flow] and 9.56 weight percent of carbon (from Chevron Chemical Company, San Ramon, Calif. under the tradename of Shawinigan Black®). About 100 grams of the resulting mixture is placed into a grinding machine (Attritor Model S-1 purchased from Union Process, Akron, Ohio) and ground for 30 minutes. Afterwards, the resulting mixture is dried at about 260° C. for 21 hours.

ii. Cathode Paste

A cathode paste is prepared by combining sufficient cathode powder to provide for a final product having 45 weight percent $V_6O_{13}$.

Specifically, 171.6 grams of a 4:1 weight ratio of propylene carbonate:triglyme is combined with 42.9 grams of polyethylene glycol diacrylate (molecular weight about 400 available as SR-344 from Sartomer Company, Inc., Exton, Pa.), and about 7.6 grams of ethoxylated trimethylolpropane triacylate (TMPEOTA) (molecular weight about 450 available as SR-454 from Sartomer Company, Inc., Exton, Pa.) in a double planetary mixer (Ross #2 mixer available from Charles Ross & Sons, Company, Hauppag, N.Y.).

A propeller mixture is inserted into the double planetary mixer and the resulting mixture is stirred at a 150 rpms until homogeneous. The resulting solution is then passed through sodiated 4 Å molecular sieves. The solution is then returned to double planetary mixer equipped with the propeller mixer and about 5 grams of polyethylene oxide (number average molecular weight about 600,000 available as Polyox WSR-205 from Union Carbide Chemicals and Plastics, Danbury, Conn.) is added to the solution vortex from by the propeller by a mini-sieve such as a 25 mesh mini-sieve commercially available as Order No. 57333-965 from VWR Scientific, San Francisco, Calif.

The solution is then heated while stirring until the temperature of the solution reaches 65° C. At this point, stirring is continued until the solution is completely clear. The propeller blade is removed and the carbon powder prepared as above is then is added as well as an additional 28.71 grams of unground carbon (from Chevron Chemical Company, San Ramon, Calif. under the tradename of Shawinigan Black®). The resulting mixture is mixed at a rate of 7.5 cycles per second for 30 minutes in the double planetary mixer. During this mixing the temperature is slowly increased to a maximum of 73° C. At this point, the mixing is reduced to 1 cycle per second the mixture slowly cooled to 40° C. to 48° C. (e.g. about 45° C.). The resulting cathode paste is maintained at this temperature until just prior to application onto the current collector.

The resulting cathode paste has the following approximate weight percent of components:

| | |
|---|---|
| $V_6O_{13}$ | 45 weight percent |
| Carbon | 10 weight percent |
| 4:1 propylene carbonate/triglyme | 34 weight percent |
| Polyethylene oxide | 1 weight percent |
| Polyethylene glycol diacrylate | 8.5 weight percent |
| ethoxylated trimethylolpropane triacrylate | 1.5 weight percent |

In an alternative embodiment, the requisite amounts of all of the solid components may be added directly to combined liquid components. In this regard, mixing speeds can be adjusted to account for the amount of the material mixed and size of vessel used to prepare the cathode paste. Such adjustments are well known to the skilled artisan.

In order to enhance the coatability of the carbon paste onto the current collector, it may be desirable to heat the paste to a temperature of from about 60° C. to about 130° C. and more preferably, from about 80° C. to about 90° C. and for a period of time of from about 0.1 to about 2 hours, more preferably, from about 0.1 to 1 hour and even more preferably from about 0.2 to 1 hour. A particularly preferred combination is to heat the paste at from about 80° C. to about 90° C. for about 0.33 to about 0.5 hours.

During this heating step, there is no need to stir or mix the paste although such stirring or mixing may be conducted during this step. However, the only requirement is that the composition be heated during this period. In this regard, the composition to be heated has a volume to surface area ratio such that the entire mass is heated during the heating step.

A further description of this heating step is set forth in U.S. patent application Ser. No. 07/968,203, filed Oct. 29, 1992, and entitled "METHODS FOR ENHANCING THE COATABILITY OF CARBON PASTES TO SUBSTRATES", which application is incorporated herein by reference in its entirety.

The so-prepared cathode paste is then placed onto the adhesion layer of the current collector described above by extrusion at a temperature of from about 45° to about 48° C. A Mylar cover sheet is then placed over the paste and the paste is spread to thickness of about 90 microns (μm) with a conventional plate and roller system and is cured by continuously passing the sheet through an electron beam apparatus (Electrocurtain, Energy Science Inc., Woburn, Mass.) at a voltage of about 175 kV and a current of about 1.0 mA and at a rate of about 1 cm/sec. After curing, the Mylar sheet is removed to provide for a solid cathode laminated to the aluminum current collector described above.

C. Electrolyte 56.51 grams of propylene carbonate, 14.13 grams of triglyme, 10.00 grams of urethane acrylate (Photomer 6140, available from Henkel Corp., Coating and Chemical Division, Ambler, Pa.) and 7.56 grams of $CH_2CHCH_2Si(O(CH_2CH_2O)_3CH_3)_3$ are combined at room temperature until homogeneous. The resulting solution is passed through a column of 4 Å to remove water and then mixed at room temperature until homogeneous.

At this point, 2.57 grams of polyethylene oxide film forming agent having a number average molecular weight of about 600,000 (available as Polyox WSR-205 from Union Carbide Chemicals and Plastics, Danbury, Conn.) is added to the solution and then dispersed while stirring with a magnetic stirrer over a period of about 120 minutes. After dispersion, the solution is heated to between 60° C. and 65° C. with stirring until the film forming agent dissolved. The solution is cooled to a temperature of between 45° and 48° C., a thermocouple is placed at the edge of the vortex created by the magnetic stirrer to monitor solution temperature, and then 9.24 grams of $LiPF_6$ is added to the solution over a 120 minute period while thoroughly mixing to ensure a substantially uniform temperature profile throughout the solution. Cooling is applied as necessary to maintain the temperature of the solution between 45° and 48° C.

In one embodiment, the polyethylene oxide film forming agent is added to the solution via a mini-sieve such as a 25 mesh mini-sieve commercially available as Order No. 57333-965 from VWR Scientific, San Francisco, Calif.

The resulting solution contains the following:

| Component Percent[2] | Amount | Weight |
| --- | --- | --- |
| Propylene carbonate | 56.51 g | 56.51 |
| Triglyme | 14.13 g | 14.13 |
| Urethane acrylate | 10.00 g | 10.00 |
| $LiPF_6$ | 9.24 g | 9.24 |
| PEO film forming agent | 2.56 g | 2.56 |
| $CH_2=CHCH_2Si(O(CH_2CH_2O)_3CH_3)_3$ | 7.56 g | 7.56 |
| Total | 100 g | 100 |

[2]=weight percent based on the total weight of the electrolyte solution (100 g).

This solution is then degassed to provide for an electrolyte solution wherein little, if any, of the $LiPF_6$ salt decomposes.

Optionally, solutions produced as above and which contains the prepolymer, the polyalkylene oxide film forming agent, the electrolyte solvent and the $LiPF_6$ salt are filtered to remove any solid particles or gels remaining in the solution. One suitable filter device is a sintered stainless steel screen having a pore size between 1 and 50 μm at 100% efficiency.

Alternatively, the electrolyte solution can be prepared in the following manner. Specifically, in this example, the mixing procedure is conducted using the following weight percent of components:

| | |
| --- | --- |
| Propylene carbonate | 52.472 weight percent |
| Triglyme | 13.099 weight percent |
| Urethane acrylate[3] | 12.819 weight percent |
| $LiPF_6$ | 10.720 weight percent |
| PEO film forming agent[4] | 3.340 weight percent |
| $CH_2=CHCH_2Si(O(CH_2CH_2O)_3CH_3)_3$ | 7.560 weight percent |

[3] (Photomer 6140, available from Henkel Corp., Coating and Chemical Division, Ambler, Pa.)
[4] Polyethylene oxide film forming agent having a number average molecular weight of about 600,000 (available as Polyox WSR-205 from Union Carbide Chemicals and Plastics, Danbury, Conn.)

The mixing procedure employs the following steps:

1. Check the moisture level of the urethane acrylate. If the moisture level is less than 100 ppm water, proceed to step 2. If not, then first dissolve the urethane acrylate at room temperature, <30° C., in the propylene carbonate and triglyme and dry the solution over sodiated 4 Å molecular sieves (Grade 514, 8–12 Mesh from Schoofs Inc., Moraga, Calif.). Add the allyl silane monomer and then proceed to step 4.

2. Dry the propylene carbonate and triglyme over sodiated 4 Å molecular sieves (Grade 514, 8–12 Mesh from Schoofs Inc., Moraga, Calif.).

3. At room temperature, <30° C., add the urethane acrylate and the allyl silane monomer to the solvent prepared in step 2. Stir at 300 rpm until the resin is completely dissolved. The solution should be clear and colorless.

4. Dry and then sift the polyethylene oxide film forming agent through a 25 mesh mini-sieve commercially available as Order No. 57333-965 from VWR Scientific, San Francisco, Calif. While stirring at 300 rpm, add the dried and pre-sifted polyethylene oxide film forming agent slowing to the solution. The polyethylene oxide film forming agent should be sifted into the center of the vortex formed by the stirring means over a 30 minute period. Addition of the polyethylene oxide film forming agent should be dispersive and, during addition, the temperature should be maintained at room temperature (<30° C.).

5. After final addition of the polyethylene oxide film forming agent, stir an additional 30 minutes to ensure that the film forming agent is substantially dispersed.

6. Heat the mixture to 68° C. to 75° C. and stir until the film forming agent has melted and the solution has become transparent to light yellow in color. Optionally, in this step, the mixture is heated to 65° C. to 68° C.

7. Cool the solution produced in step 6 and when the temperature of the solution reaches 40° C. add the $LiPF_6$ salt very slowly making sure that the maximum temperature does not exceed 55° C.

8. After the final addition of the $LiPF_6$ salt, stir for an additional 30 minutes, degas, and let sit overnight and cool.

9. Filter the solution through a sintered stainless steel screen having a pore size between 1 and 50 μm at 100% efficiency.

At all times, the temperature of the solution should be monitored with a thermocouple which should be placed in the vortex formed by the mixer.

Afterwards, the electrolyte mixture is then coated by a conventional knife blade to a thickness of about 50 μm onto the surface of the cathode sheet prepared as above (on the side opposite that of the current collector) but without the Mylar covering. The electrolyte is then cured by continuously passing the sheet through an electron beam apparatus (Electrocurtain, Energy Science Inc., Woburn, Mass.) at a voltage of about 175 kV and a current of about 1.0 mA and at a conveyor speed setting of 50 which provides for a conveyor speed of about 1 cm/sec. After curing, a composite is recovered which contained a solid electrolyte laminated to a solid cathode.

D. Anode

The anode comprises a sheet of lithium foil (about 76 μm thick) which is commercially available from FMC Corporation Lithium Division, Bessemer City, N.C.

E. The Solid Electrolytic Cell

A sheet comprising a solid battery is prepared by laminating the lithium foil anode to the surface of the electrolyte in the sheet produced in step C above. Lamination is accomplished by minimal pressure.

Without being limited thereby, it is believed that the incorporation of the allyl silane monomers of the invention into the polymer backbone of the solid polymeric matrix provides the following advantages.

First, by providing up to three reactive sites on the Si atom it is possible to provide up to two additional pendant groups compared with, for example, an acrylate. If the pendant groups are selected from a glyme, a carbonate or another compound containing a heteroatom, it is believed that the conductivity of the solid polymeric matrix may be correspondingly increased.

Second, if the pendant groups $R_1$, $R_2$ and $R_3$ include polyalkylene ether groups (e.g., glyme, diglyme, etc.), the compatibility of the solid polymeric matrix and the inorganic ion salt is significantly increased by increasing the solubility of the inorganic ion salt in the matrix.

Third, the additional pendant groups allow the solid polymeric matrix to "open up", such that the polymer chains are more spread out. This gives the polymer greater flexibility and swellability. If cross-link density of the polymer matrix is too high, resulting in a tightly bound polymer, one or more of the arms (i.e., pendant silane groups) may become entangled in the cross-link, but the remaining arm or arms are still available for coordination with an inorganic ion.

By comparison, for acrylic groups, since only one pendant group or arm is available for coordination, if it becomes entangled, then no pendant groups are available for ion transport.

Another advantage, in the embodiment in which an inorganic ion is incorporated into the pendant group or groups to form an ion salt derivative, is that it is possible to eliminate the use of the inorganic ion salt per se.

What is claimed is:

1. A compound represented by Formula I:

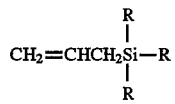

where R is selected from the group consisting of —O(CH$_2$CH$_2$O)$_3$CH$_3$ and —O(CH$_2$CH$_2$O)Li.

2. A compound according to claim 1, wherein R is —O(CH$_2$CH$_2$O)$_3$CH$_3$.

3. A compound according to claim 1, wherein R is —O(CH$_2$CH$_2$O)$_3$Li.

4. A single phase, solid, solvent-containing electrolyte which comprises:

a solid polymeric matrix; and an electrolyte solvent;

wherein said solid polymeric matrix is obtained by copolymerizing an allyl silane monomer represented by Formula I:

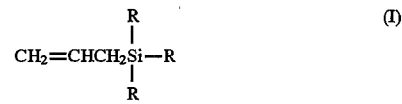

where R is selected from the group consisting of —O(CH$_2$CH$_2$O)$_3$CH$_3$ and —OC(CH$_2$CH$_2$O)Li.

5. A single phase, solid, solvent-containing electrolyte according to claim 4, where R is —O(CH$_2$CH$_2$O)$_3$CH$_3$.

6. A single phase, solid, solvent-containing electrolyte according to claim 4, where R is —O(CH$_2$CH$_2$O)$_3$Li.

7. A single phase, solid, solvent-containing electrolyte according to claim 4, wherein said electrolyte solvent comprises a mixture of propylene carbonate and triglyme.

8. A single phase, solid, solvent-containing electrolyte according to claim 4, further including an ion conducting amount of LiPF$_6$.

9. A single phase, solid, solvent-containing electrolyte according to claim 4, further including urethane acrylate comonomer in said solid polymeric matrix.

10. An electrolytic cell which comprises:

an anode comprising a compatible anodic material; a cathode comprising a compatible cathodic material; and interposed therebetween a single phase, solid, solvent-containing electrolyte which comprises:

a solid polymeric matrix; and an electrolyte solvent;

wherein said solid polymeric matrix is obtained by polymerizing or copolymerizing an allyl silane monomer represented by Formula I:

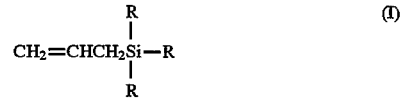

where R is selected from the group consisting of —O(CH$_2$CH$_2$O)$_3$CH$_3$ and —O(CH$_2$CH$_2$O)$_3$Li.

11. An electrolytic cell according to claim 10, wherein R is —O(CH$_2$CH$_2$O)$_3$CH$_3$.

12. An electrolytic cell according to claim 10, where R is —O(CH$_2$CH$_2$O)$_3$Li.

13. An electrolytic cell according to claim 10, wherein said electrolyte solvent comprises a mixture of propylene carbonate and triglyme.

14. An electrolytic cell according to claim 10, further including in said electrolyte an ion conducting amount of LiPF$_6$.

15. An electrolytic cell according to claim 10, further including urethane acrylate comonomer in said solid polymeric matrix.

* * * * *